US006277259B1

United States Patent
Guttman et al.

(10) Patent No.: US 6,277,259 B1
(45) Date of Patent: Aug. 21, 2001

(54) HIGH PERFORMANCE MULTIDIMENSIONAL PROTEOME ANALYZER

(75) Inventors: Andras Guttman, Irvine; Laszlo Takacs, Newberry Park, both of CA (US)

(73) Assignees: Enterprise Partners II, La Jolla; Indosuez Investment Management Services, Inc., Menlo Park, both of CA (US)

( * ) Notice: Subject to any disclaimer, the term of this patent is extended or adjusted under 35 U.S.C. 154(b) by 0 days.

(21) Appl. No.: 09/298,800

(22) Filed: Apr. 23, 1999

Related U.S. Application Data

(60) Provisional application No. 60/083,016, filed on Apr. 24, 1998.

(51) Int. Cl.[7] .......................... G01N 27/26; G01N 27/447
(52) U.S. Cl. .......................... 204/461; 204/456; 204/459; 204/466; 204/467; 204/606; 204/610; 204/612; 204/616; 204/618
(58) Field of Search ........................................ 204/606, 610, 204/612, 616, 618, 456, 459, 466, 467, 461

(56) References Cited

U.S. PATENT DOCUMENTS 5,320,727 * 6/1994 Jackson ................................ 204/459
5,637,202 * 6/1997 Harrington et al. ............. 204/606 X

* cited by examiner

Primary Examiner—Jill Warden
Assistant Examiner—John S. Starsiak, Jr.
(74) Attorney, Agent, or Firm—Lyon & Lyon LLP

(57) ABSTRACT

A proteome analyzer includes a separation cassette having a first dimension separation compartment for separation of protein samples by isoelectric focusing and a second dimension separation compartment for separation of protein samples by SDS-polymer network electrophoresis. The first dimension compartment is a reservoir in which a porous material having capillary channels is disposed. The protein samples are disposed in the capillary channels and, in the presence of a pH gradient, are focused spatially by isoelectric focusing upon application of an electric field. The second dimension separation compartment consists of two glass or plastic plates separated by a separation medium. The separation medium is an ultra-thin layer of a low concentration linear polymer supported by an inert matrix. The spatially focused protein samples are contacted with the separation medium in the presence of an electric field to initiate second dimension separation. The migrating SDS-protein complexes are fluorescently labeled by a dye in the separation medium during second dimension separation, and are detected by an illumination and detection system as they pass through a detection area. The detected SDS-protein complexes are imaged and displayed by computer analysis as two-dimensional maps representing the proteins in the sample.

29 Claims, 3 Drawing Sheets

TWO DIMENSIONAL ULTRATHIN SEPARATION OF PROTEIN MIXTURE
WITH REAL TIME FLUORESCENCE LABELING AND IMAGING

HIGH PERFORMANCE MULTIDIMENSIONAL PROTEOME ANALYZER

CROSS-REFERENCE TO RELATED APPLICATION

This application claims the benefit of copending U.S. Provisional Application No. 60/083,016, filed on Apr. 24, 1998.

BACKGROUND OF THE INVENTION

Today, most clinical laboratory tests are individual tests that analyze and quantify the level of a specific protein in a clinical sample such as a bodily fluid proteome (BFP). The effectiveness of proteome analysis is dependent upon the electrophoretic separation technology utilized. Most commonly, one-dimensional eletrophoretic separation methods, such as polyacrylamide gel electrophoresis, are utilized. One-dimensional separation typically resolves about 100 distinct zones per gel.

The advent of the Age of Genomics, however, has increased the perception of what is required in the post-genome era. DNA sequencing information alone cannot accurately predict many critical events. These include whether and when gene products are translated, the relative concentration of gene products, the extent of post-translational modifications of the gene products, and the effects of under- or over-expression. In cellular systems, particularly those subject to changes in physiological condition or disease, dynamic genome activity, such as up- and down-regulation, can cause the appearance and disappearance of hundreds or thousands of spots per electrophoretic image. The changes reflected in the electrophoretic image must be evaluated and analyzed quantitatively by a high performance image-processing algorithm. To adequately decipher multigenic phenomena and interactions between genes, the sensitivity of the analysis system should permit simultaneous, quantitative tracking of 40–70% of all genome activity.

Two- or multi-dimensional separation methods allow specific recognition of nearly all detectable protein spots in a BFP. Multi-dimensional electric field mediated analysis yields resolutions of up to tens of thousands of distinct zones per gel. Hence, multi-dimensional separation is far superior to one-dimensional separation for separation of complex mixtures of protein molecules and for tracking multigenic phenomena at the cell, tissue and even organism level.

Although two-dimensional separation technology is twenty years old, employment of the technology has been hindered by a number of obstacles. These include an inability to produce consistent results from the same samples, and a lack of an adequate method for analysis of the plethora of information generated by multi-dimensional analysis. Often, analysis of a two-dimensional separation pattern consists simply of holding two gels up to a light and, unless differences are visible in the peripheries of the gels, disposing of the bulk information the gels represent. Another major obstacle, relating to the lack of an adequate analysis method, is the absence of a simple system to identify and quantify individual proteins or groups of proteins. Moreover, despite numerous refinements in electrophoretic techniques over the past decade, two-dimensional separation is still tedious and inefficient. The time required to prepare, load, separate and visualize complex mixtures of protein molecules is substantial. This is especially problematic, since throughput is the single most important factor influencing the cost effectiveness of proteome analysis. Though automated laboratory analyzers simplify these complex tasks with robotics, robotics are not cost effective in small outpatient health care units.

Despite these problems, electric field mediated two-dimensional separation methods, such as two-dimensional gel electrophoresis, continue to gain importance in biological research and direct clinical applications. One reason is the perceived potential to identify certain protein molecules or groups of proteins that are up- or down regulated, and whose concentration can be correlated with a disease and ration varies with the disease progress.

Conventional two-dimensional gel electrophoresis-based protein separation methods comprise two separation dimensions: isoelectric focusing, ("IEF") and sodium dodecyl sulfate-polyacrylamide gel electrophoresis ("SDS-PAGE"). IEF is almost exclusively the first separation dimension. In IEF, amphoteric molecules such as proteins are separated by electrophoresis in a pH gradient generated between a cathode and an anode. IEF takes advantage of the fact that each protein has a characteristic pH at which it is electrically neutral. This characteristic pH is the isoelectric point (pI) of the protein. Under the influence of an electric field, charged sample components migrate through an electrophoresis medium (a solution or a gel). If a sample component has a net negative charge, it migrates towards the anode. During migration, the negatively charged sample encounters a progressively lower pH, thus becoming more positively charged. Eventually, the pI is reached where the net charge of the sample component is zero. At the pI, migration stops and the sample component is "focused" in a tight zone. Likewise, if a sample component is positively charged, it will migrate towards the cathode. In this manner, each sample component migrates to its isoelectric point. IEF is a true electric field mediated focusing technique since protein molecules that diffuse out of the focused zone acquire charge and are pulled back into the zone where the net charge is zero.

The pH gradient, which is key to the success of IEF, is provided by molecules called "carrier ampholites". Carrier ampholites are polyamino-polycarboxic acids having gradually differing pI values. Ampholite mixtures are available in various narrow and broad pH ranges. Typically, an anticonvective media such as polyacrylamide or agarose is used. It is also possible to immobilize pH gradients on a suitable matrix such as polyacrylamide or ampholite strips. With immobilized pH gradients, IEF routinely provides a resolution of 0.1 to 0.01 pI units.

Relatively high electric field strengths are necessary to obtain rapid isoelectric focusing. Use of capillary dimensions (i.e. dimensions less than 0.2 mm I.D.) provides efficient dissipation of Joule heat and permits the use of such high field strengths. In capillary dimensions, IEF separations can be carried out in free solution or in entangled polymer networks.

As noted above, the second separation dimension is typically carried out by SDS-PAGE. SDS-PAGE involves complex relationships among several factors. These factors include separation length, gel composition, gel pore size, electric field strength, ionic moiety, buffer composition and the mode of migration of the polyion through the gel matrix. In conventional SDS-PAGE separations, biopolymers migrate under the influence of an electric field by tumbling through pores whose average radii are much larger that the radius of gyration of the analyte. Migrating samples are thereby size-ordered based on the time required to find a path through the pores of the gel matrix. This type of migration is known as separation in the Ogston regime, and is usually quite time-consuming. Larger molecules, i.e. those molecules whose radii of gyration are larger than the average pore size, are impeded and become oriented towards the electric field while migrating through the pores. This process, which is called reptation, can be induced through increases in either the gel concentration or the applied electric field strength.

The use of increased electric field strengths (typically greater than 100V/cm) necessitates thickness reduction in planar systems. Thickness reduction enhances the ability to dissipate heat and thereby reduces the effects of Joule heat. Some emerging capillary electrophoresis methods employ narrow-bore capillary columns having large surface-to-volume ratios to effectively dissipate heat. In planar electrophoretic systems, the surface-to-volume ratio is increased through thickness reduction, ideally converging towards capillary dimensions. This is known as "ultra-thin" gel electrophoresis. Rapid biopolymer separation, for example, requires gel-filled separation platforms having a thickness of no more than 0.25 mm. The use of 0.1 mm thick gels for biopolymer separation allows as much as a five-fold increase in electric field strength. Use of polyacrylamide gels having a thickness of 0.025 to 0.1 mm permits resolution of complex mixtures of DNA sequencing reactions in less than 30 minutes.

The most recent advances in electrophoretic separation have been in methods such as capillary electrophoresis and in novel composite separation matrices. First, crosslinked polyacrylamide-polyethylene glycol copolymers were used to achieve size separation of SDS-protein molecules. Later, linear polymers such as non-crosslinked polyacrylamide, dextran and polyethylene oxides were shown to be effective, on a basis of chain-length, when subjected to an electric field. The use of non-crosslinked polymers has been primarily in high performance capillary electrophoresis applications, although high concentrations of non-crosslinked polymers can be used in planar formats to obtain separation of restriction fragments. Use of non-crosslinked polymers is advantageous in several respects. Non-crosslinked polymers may be supplied in a dessicated dry form, thereby providing a practically unlimited shelf life. Planar non-crosslinked polymer gels can be easily re-hydrated to any final gel concentration, buffer composition or strength.

The separation length necessary for resolution of protein molecules in planar ultra-thin gel electrophoresis is constantly being adjusted downward. Efforts to optimize electrophoresis separation media and techniques originated in the early 1960s when micro methods were described as micro-electrophoresis. Imaging technologies existing at that time, however, could not capture separations on such a minute scale. As imaging technology has evolved to the point where exploitation of micro-electrophoretic methods might be possible, these methods had been virtually forgotten.

Currently, there are many techniques for detection and visualization of protein molecules separated by gel electrophoresis. Among them are staining techniques based on Coomassie Brilliant Blue R-250, Amido Black, Ponceau S, Fast green and silver staining. Fluorophore labeling of the separated protein spots with dyes such as Ethidium Bromide, Nile Red and Sypro Orange/Red has also been introduced recently. The use of several different fluorophores, each of which is differentiable by its spectral characteristics, has increased the precision of run-to-run reproducibility. Detection of stained spots is currently done by eye, by scanners or by so-called "camera on the stick" devices.

Analysis of the data generated by electrophoresis involves spot detection based on convolutions or filtrations of image gray levels. Conventional systems first identify a spot's center of gravity or peak maximums before defining other spot parameters. A given pixel and its neighbors are taken into account by thresholding edge detection and region growing or neighborhood analysis by Laplacian, Gaussian, etc. operators. Spot detection by threshold analysis, edge detection, erosion and dilation can also be employed to deconvolute comigrating spot boundaries, although this is probably best achieved by post-separation analysis. Pattern recognition software allows real-time comparison of protein maps with databases comprised of large numbers of gels, each of which may contain hundreds or thousands of protein spots. Currently available two-dimensional analysis systems include the PC software-based Phoretix 2-D and Melanie II systems.

Two-dimensional electrophoresis technology has the potential to further medical research and diagnosis by providing quantitative and qualitative identification of gene expression differences as well as characterization of specific cancer cell proteomes. The complex, labor-intensive, time-consuming and non-standardized nature of the available technology, however, has curtailed its use in both research and clinical laboratory settings. Accordingly, there is a need for a multi-dimensional electric field mediated proteome analyzer that overcomes the drawbacks of the prior art.

SUMMARY OF THE INVENTION

In accordance with the purpose of the invention as broadly described herein, there is provided a high performance, multi-dimensional proteome analyzer. The automated analyzer allows, through standardized generation of BFP, quantification of all detectable proteins in complex clinical samples. The analysis sensitivity is equal to or exceeds that of existing immunoassays. One test using the inventive analyzer takes about 30–60 minutes, including computation time, and displays all detectable proteins at the desired level of sensitivity. Results are provided quickly and do not require a fully equipped clinical laboratory or specially trained personnel. Similarly to X-ray images, images are stored in an electronic format for future reference and potential retrospective analysis. The low equipment and per-test cost of the analyzer makes its use in small outpatient patient health care units realistic.

The analyzer incorporates an electric field mediated separation device that is capable of multi-dimensional separation and comparative analysis of biological samples composed of complex mixtures of proteins and peptides. The analysis is based on differences in physical and chemical properties of analyte molecules. Spectral characteristics and differences of multicolor labeled sample BFP and control BFP (c-BFP) or other controls are measured. BFP and c-BFP are detected simultaneously using an illumination and detection system, and are analyzed and evaluated in real time with a high performance registration algorithm.

In one embodiment of the present invention, an automated and integrated proteome analyzer is provided. The analyzer comprises a separation cassette for providing two-dimensional separation of a sample; an illumination and detection system for illuminating and detecting the separated proteinaceous sample during second dimension separation; and an analysis system for processing data received from the illumination and detection system and formatting the data into a two-dimensional map representing the separated proteinaceous sample. The separation cassette includes a first dimension separation compartment housing a material having capillary channels. The proteinaceous sample is disposed in the capillary channels for first dimension separation in the presence of a pH gradient. The cassette also includes a second dimension separation compartment housing a separation medium that receives the proteinaceous sample for second dimension separation. A power supply is configured to apply an electric field across either the first dimension compartment or the second dimension compartment for first or second dimension separation.

In another embodiment of the present invention, a separation cassette for providing two-dimensional separation comprises first and second reservoirs. The first reservoir is a first dimension separation compartment and contains a porous material having capillary channels. A proteinaceous sample is absorbed in the porous material, and a pH gradient is disposed in the first reservoir. A second dimension separation compartment is fluidly connected to the first and second reservoirs. The second dimension compartment comprises two glass or plastic plates separated by an ultra-thin layer of a linear polymer suspended in an inert matrix. A power supply is configured to apply an electric field across either the first reservoir to effect isolectric focusing or across the second dimension separation compartment to effect separation by a sieving effect.

In one implementation of this embodiment, the separation cassette is integrated with an illumination and detection system and an analysis system. The illumination and detection system comprises a laser for emitting an illuminating beam and a lens set for focusing the illuminating beam on a detection area of the second dimension separation compartment. An illumination fiber transmits the illuminating beam from the laser to the lens set, which is oscillated over the detection area by a translation stage. Collection fibers collect the fluorescent light emitted by the separated proteinaceous sample and transmit the light to an avalanche photodiode detector, which supplies data to the analysis system.

In a further embodiment of the present invention, a method for analyzing a proteinaceous sample by two-dimensional separation is provided. The method comprises the following steps:

(a) disposing the proteinaceous sample in a material having capillary channels;

(b) disposing the material having capillary channels in a pH gradient;

(c) applying a first electric field to the material to effect a first dimension separation by isoelectric focusing of components of the proteinaceous sample;

(d) contacting the material containing the focused proteinaceous sample with a separation medium;

(e) applying a second electric field to the separation medium to effect a second dimension separation of the proteinaceous sample;

(f) fluorescently labeling the proteinaceous sample during second dimension separation;

(g) illuminating the fluorescently labeled sample;

(h) collecting light emitted by the fluorescently labeled sample; and (i) analyzing the collected light and formatting a two-dimensional image map corresponding to the separated proteinaceous sample.

Objects and advantages of the present invention include any of the foregoing, singly or in combination. Further objects and advantages will be apparent to those of ordinary skill in the art, or will be set forth in the following disclosure.

BRIEF DESCRIPTION OF THE DRAWINGS

The present invention is described with reference to the accompanying drawings. In the drawings, like reference numbers indicate identical or functionally similar elements.

DETAILED DESCRIPTION OF PREFERRED EMBODIMENTS

Figure 1:
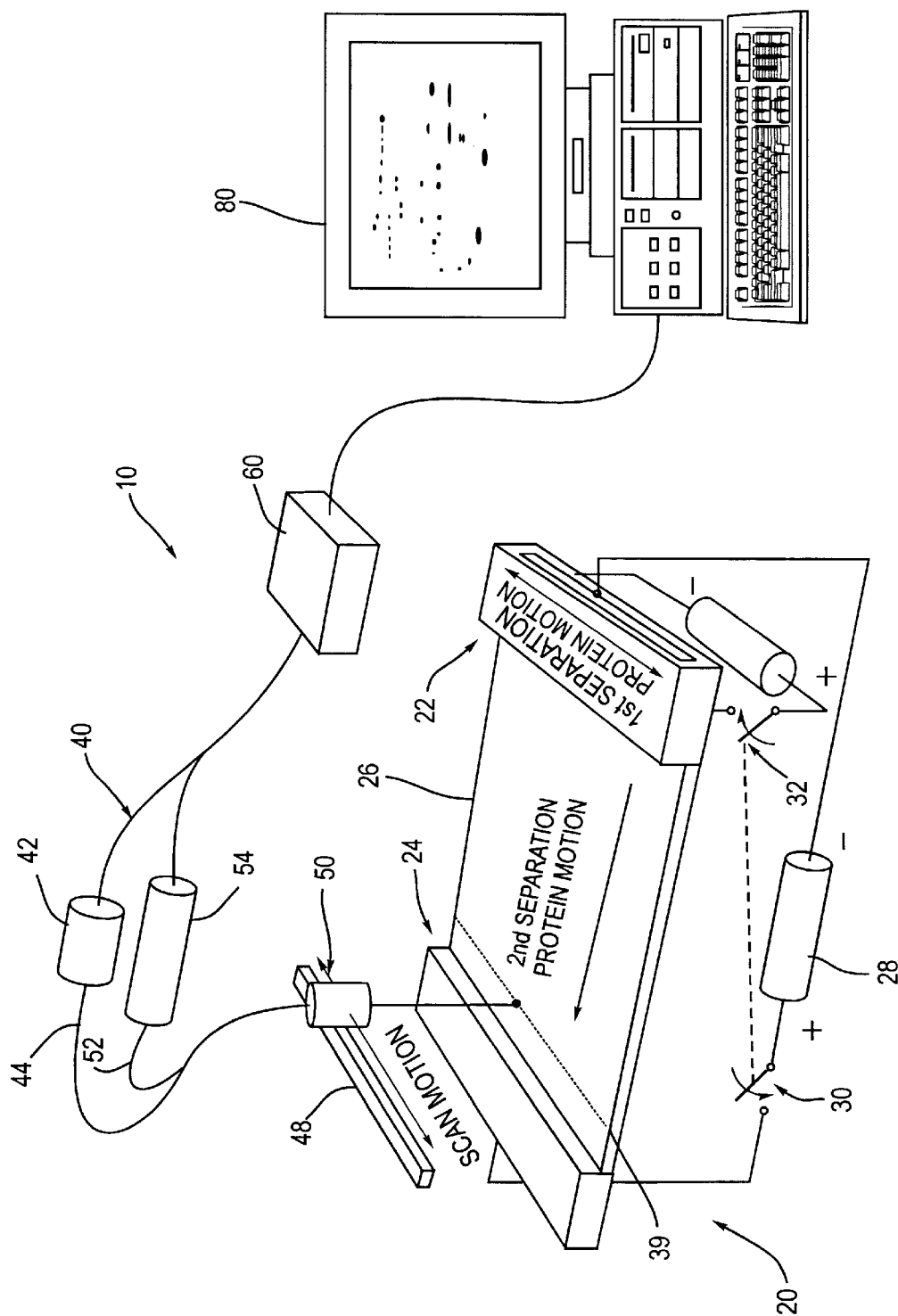
FIG. 1 is a perspective view of a proteome analyzer according to the present invention.

FIG. 1 illustrates a high performance multi-dimensional proteome analyzer 10. Analyzer 10 comprises a separation cassette 20, an illumination and detection system 40, interface electronics block 60 and a computer 80.

Separation cassette 20 is a horizontal ultra-thin layer electrophoresis platform. Positional heat sinks (not shown) support cassette 20 and provide temperature control during separation. The heat sinks are typically a heat dissipative material such as aluminum that eliminates separation irregularities by dissipating any extra heat generated during separation. When cassette 20 is positioned, it makes contact with platinum or gold-plated beryllium electrodes to complete the circuit for both dimensional separations (see FIGS. 2a and 2b and description below). A thermoelectric device (not shown) may also be provided for temperature control.

Separation cassette 20 includes first-dimensional separation compartments 22 and 24 fluidly connected by a second-dimensional separation compartment 26. First-dimensional separation compartments 22 and 24 take the form of buffer reservoirs, and second-dimensional separation compartment 26 takes the form of two substantially planar glass or plastic plates with a separation medium therebetween. The separation medium is preferably an ultra-thin layer of a low concentration linear polymer suspended in an inert support matrix. A high voltage power supply 28 is configured with switches 30 and 32 to permit application of a high power electric field across either the second-dimensional compartment (switch 30 closed) or across first-dimensional reservoir 22 (switch 32 closed).

Figures 2A, 2B:
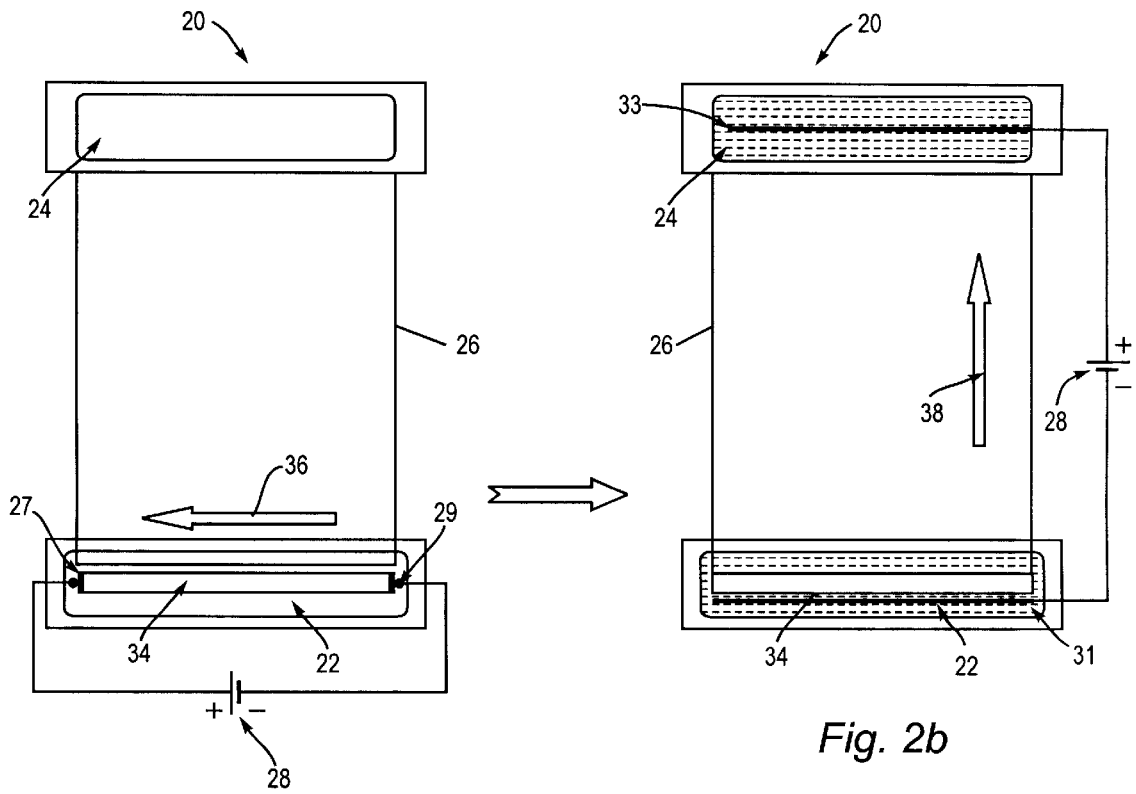
FIG. 2a is a top view of a cassette portion of the analyzer of FIG. 1 during first dimension separation.
FIG. 2b is a top view of the cassette during second dimension separation.

FIG. 2a depicts first-dimensional separation by isoelectric focusing (IEF). An IEF separation material 34 is disposed in reservoir 22. The separation material may be any porous material, matrix or medium that has capillary channels. Agarose and porous membranes or loaders are examples of suitable materials that provide capillary channels. In the case of a porous membrane, the membrane is soaked in a sample proteinaceous mixture, and is disposed or soaked in an appropriate (standard or immobilized) pH gradient. If an alternate material providing capillary channels is utilized, such as agarose, a protein and pH gradient mixture may be injected directly into a reservoir partially filled with the capillary channel material.

Power supply 28 is connected across electrodes 27 and 29 positioned at opposite ends of porous material 34. When an electric field is applied by power supply 28 across reservoir 22 in the direction indicated by arrow 36, the individual components of the sample begin to focus spatially (move to their isoelectric points) through the capillary channels of the porous material. Alternatively, single-capillary IEF that mimics the multiple capillary structure of a porous material could be used as the first dimension. A significant drop in electric current indicates that the sample components have moved to their isoelectric points and that first dimensional IEF separation is complete.

Although first dimension separation by IEF is preferred, alternative electric field mediated separation methods could be utilized. Examples of alternate separation methods include SDS-PAGE, zone electrophoresis, micellar electrokinetic chromatography, affinity electrophoresis and electrochromatography.

After IEF separation, power supply 28 is removed from reservoir 22. Membrane 34 is placed in intimate proximity to the separation medium in second dimensional separation compartment 26 to serve as an injection medium for second dimension separation. As noted above, separation compartment 26 consists of two planar glass or plastic plates separated by a separation medium. The separation medium is preferably an ultra-thin layer of a low concentration linear polymer supported by an inert matrix. Preferably, the thickness of the layer is less than 0.2 mm. Power supply 28 is connected across electrodes 31 and 33 positioned on reservoirs 22 and 24 to initiate second-dimension separation (FIG. 2b). An electric field is applied across compartment 26 in the direction indicated by arrow 38 (from IEF separation reservoir 22 towards reservoir 24). SDS molecules from the separation medium migrate into the focused sample zones in the porous material, forming SDS-protein complexes with the individual protein molecules and dragging the molecules into second dimension separation compartment 26.

Second dimensional compartment 26 is appropriately coated (hydrophilic, e.g., linear polyacrylamide) and, in conjunction with an appropriate separation medium, rapidly separates SDS-protein complexes by their molecular weight. The separation mechanism is based on a sieving effect that occurs as the SDS-protein complexes pass through a linear polymer suspended in an inert matrix. Suitable linear polymers include, but are not limited to, non-cross linked polyacrylamide, dextran, polyethylene oxides, derivatized celluloses and polyvinylpyrrolidone or mixtures thereof. The linear polymer concentration should be less than 25%. The linear polymer is suspended in an inert support matrix to prevent flow (convection) of the linear polymer. Suitable materials for the matrix include, but are not limited to, agarose and micro-lithographic arrays. Due to the capillary dimensions of the ultrathin layer separation cassette, a high separation voltage can be applied, similar to capillary electrophoresis, to assure fast and efficient separation. In addition, the ultra-thin format enhances dissipation of Joule heat that develops during separation.

Though second dimension separation as described above is preferred, other electric field mediated separation methods could be utilized. Alternate separation methods include, but are not limited to, isoelectric focusing, zone electrophoresis, micellar electrokinetic chromatography, affinity electrophoresis and electro-chromatography.

During second dimension separation, the migrating samples are stained "in migratio" by complexation with a complexing dye incorporated directly into the separation medium. In addition to conventional covalent fluorophore labeling, the use of fluorescent affinity ligands in the separation medium expands detection sensitivity and separation potential. The positive charge of complexing dye molecules (e.g., Ethidium Bromide, Sypro dyes) can significantly affect the migration velocity of the protein molecules relative to the biopolymer-stain complex. Hence, the complex formation with fluorescent stain permits high sensitivity fluorescence-detection of the migrating protein molecules and can be utilized to achieve higher resolution. When the complexing dye is incorporated into the separation matrix, high resolution of closely migrating fragments is achieved in a broad molecular weight range of 20–200 kDaltons.

The mechanism whereby protein molecules migrate in the separation matrix in the presence of the complexing dye is very complex. The stain, as a complexing ligand ($L^+$) binds to the SDS-covered polypeptide chains ($P^{n-}$). Due to its positive charge, it decreases the electrophoretic mobility of the protein-stain complex ($PL_m^{(n-m)-}$) by reducing the overall charge:

$$P^{n-} + mL^+ = PL_m^{(n-m)-};  \quad (eq.\ 1)$$

and $$K = \frac{PL_m^{(n-m)-}}{(P^{n-})(L^+)^m}; \quad (eq.\ 2)$$

where K is the formation constant of the complex, m is the number of the positively charged stain molecules in the complex, and n is the total number of negative charges on the protein molecules.

The velocity (v) of the polyion complex in gel electrophoresis can be expressed as:

$$v = \frac{l}{t_m} = \mu_p E R_p; \quad (eq.\ 3)$$

where l is the effective separation length, $t_m$ is the migration time of the solute (from the injection point to the detection point), $\mu_p$ is the electrophoretic mobility of the polyion, and E is the applied electric field strength. $R_p$ is the molar ratio of the free polyion and can be expressed as:

$$R_p = \frac{P^{n-}}{c_p} = \frac{1}{1 + K(L^+)^m}; \quad (eq.\ 4)$$

where $c_p$ is the total concentration of the polyion, P.

Combining equations 3 and 4 yields equation 5, which expresses the resultant velocity of the negatively charged polyion complex in the presence of the positively charged ligand (protein stain) as:

$$v = \frac{\mu_p E}{1 + K(L^+)^m}. \quad (eq.\ 5)$$

Equation 5 illustrates that an increase in the complex formation constant and/or the concentration of the ligand leads to decreasing migration velocity of the SDS-protein-ligand complex. When $K(L^+)^m >> 1$, the electrophoretic velocity of the complex can be expressed as:

$$v = \frac{\mu_p E}{K(L^+)^m}. \quad (eq.\ 6)$$

The concentration and type of complexing dye should be selected in conjunction with the laser used in the illuminating and detection system. For a 532-nm NdYAG laser, Ethidium bromide, Nile Red, Sypro Orange and Sypro Red dyes provide optimal labeling of protein molecules.

The ability to double, triple or even quadruple the number of useable positions in the separation gel, by separating all dye-specific labeled proteins even in a single spot, would result in measurable gain in throughput and precision. In the present invention, a single dye format is employed with the possibility of using protein complexing dyes for "in migratio" labeling of protein molecules. This approach is beneficial in several ways. Unlabeled protein molecules are simply injected into the first dimensional separation reservoir and are labeled during second dimensional separation. Additionally, the complexation of the protein molecules with the labeling dye has the effect of increasing separation selectivity and resolution.

An alternative "double staining" procedure combines covalent fluorescent labeling with the "in migratio" staining procedure described above. After first dimensional separation by IEF, a fluorophore label "A" is covalently attached to homogeneously label a single protein or complex mixtures of proteins (e.g. p53, prostate specific antigens, etc.). If a separation method other than IEF is utilized, it may be possible to attach the fluorophore label before first dimension separation. The "A" fluorophore should have fluorescent characteristics close to those of the second dimensional dyes. Suitable fluorophores include, but are not limited to, Alexa 532, tetramethylrodamine, Texas Red and R6G.

After labeling with fluorophore "A", the labeled protein is mixed with a complex analyte, e.g. tumor cell lysate, serum, urine or cerebrospinal fluid. Second dimension SDS-PAGE separation is then commenced where the proteins are labeled a second time "in migratio" with a dye "B". The resulting proteome map corresponding to the covalently labeled protein emits light with spectral characteristics of fluorescent dye A+B. If the analyte does not contain any protein corresponding to the covalently stained spot, staining by dye A+B will generate a ratio of light detectable by measurements at the two, different spectral emittence maxima of dyes A and B. This ratio will change if the analyte contains any detectable amount of the protein corresponding to the covalently stained spot, generating a spot at the same coordinates where the covalently stained protein spot appears. In this case, the A/B ratio will decrease because the protein spot from the analyte will be stained by dye B only during "in migratio" staining. Spectral analysis of the spot and comparison to experimentally obtained titration curves allows precise quantitative measurement.

Another application of double staining is covalent labeling of an entire sample, a complex protein mixture, e.g. proteins prepared from normal cells, or serum, urine and cerebrospinal fluid proteins from healthy individuals. Mixing and analysis of this complex mixture to an analyte obtained from malignant cells or diseased individuals will generate a two-dimensional proteome map where each protein spot that is represented in the two samples at relatively equal levels will generate an identical spectral ratio. Those protein spots where the analyte contains an induced protein will generate a decreased A/B ratio, while those spots where the analyte contains a lower amount of protein will generate an increased A/B ratio relative to those proteins that did not change. Computational analysis of all analyzable spots allows quantification of changes in the entire proteomes and generates significant amounts of both clinical and research data.

During second dimension separation, illumination and detection system 40 (FIG. 1) scans the separation medium along a detection area or window 39. Stained SDS-protein complexes migrating through area 39 are illuminated and detected data is relayed via interface network 60 to computer 80 for analysis. Illuminating and detection system 40 comprises a laser 42 (preferably a 532-nm NdYAG laser) that emits an illuminating beam through a central illumination or detection fiber 44 to lens set 46. Lens set 46 focuses the illuminating beam on detection area 39. Lens set 46 is mounted to a translation stage 48 that moves the lens back and forth in the direction of arrow 50 to scan the illuminating beam across the detection area. Labeled sample components passing through the detection area are illuminated, and the fluorescent light emitted by the labeled sample components is collected by collection fibers 52. Collection fibers 52 forward the emitted light to light detector 54 (preferably an avalanche photodiode), which relays the imagery data to computer 80 via interface block 60. A more detailed description of a fiber optics-based integrated laser-induced fluorescence avalanche photodiode detection system is set forth in U.S. patent application Ser. No. 08/774,023, of common assignee.

Though system 40 as described above is preferred, alternative systems could be used to illuminate and detect the fluorescently labeled SDS-protein complexes. One alternative is a CCD camera-based hyper-spectral imaging system.

Computer 80 is preferably a PC having data analysis software that processes the output imagery data collected from the detector and formats the data into a digital two-dimensional map representing the proteins in the sample. The analysis is based on differences in physical and chemical properties of analyte molecules. Spectral characteristics and differences of multicolor labeled sample BFP and control BFP (c-BFP) or other controls are measured. MATLAB is preferred for real time analysis and rapid prototyping and evaluation of registration algorithms. Output data can be evaluated by appropriate bioinformatics software packages and, if desired, uploaded to the relevant Internet databases.

Analyzer 10 allows, through standardized generation of BFP, quantification of all detectable proteins in complex clinical samples. The sensitivity of analyzer 10 is equal to or exceeds that of existing immunoassays. One test using analyzer 10 takes about 30–60 minutes, including computation time, and displays all detectable proteins at the desired level of sensitivity. Results are provided quickly and do not require a fully equipped clinical laboratory or specially trained personnel. Similarly to X-ray images, images are stored in an electronic format for future reference and potential retrospective analysis. The low equipment and per-test cost of the analyzer makes its use in small outpatient patient health care units realistic.

An experiment was conducted in which a three-protein test mixture of alpha lactalbumin ($\alpha$LA), ovalbumin (OVA) and bovine serum albumin (BSA) was separated by the inventive proteome analyzer. A separation cassette having dimensions 7.5 cm×10 cm ×190 $\mu$m was utilized. The lens set of the illumination and detection system was positioned over a detection area of the second dimension separation compartment located six centimeters from the IEF separation reservoir and four centimeters from the opposing reservoir.

A separation medium was formed by combining five ml of 4% linear polyacrylamide (MW 700,000–1,000,000, Polysciences) with 5 ml of 2% melted agarose (60° C., Agarose-III, Amresco, Solon, OH) in a 100 mM Tris-Tricine buffer, pH 8.4) and 50 $\mu$l of 10% SDS and 20 $\mu$l 5× Sypro Red fluorescent dye. The cassette was preheated to 45–50° C. The separation medium was filled into the cassette in a way that the melted agarose filled half of each buffer reservoir.

Figure 3:
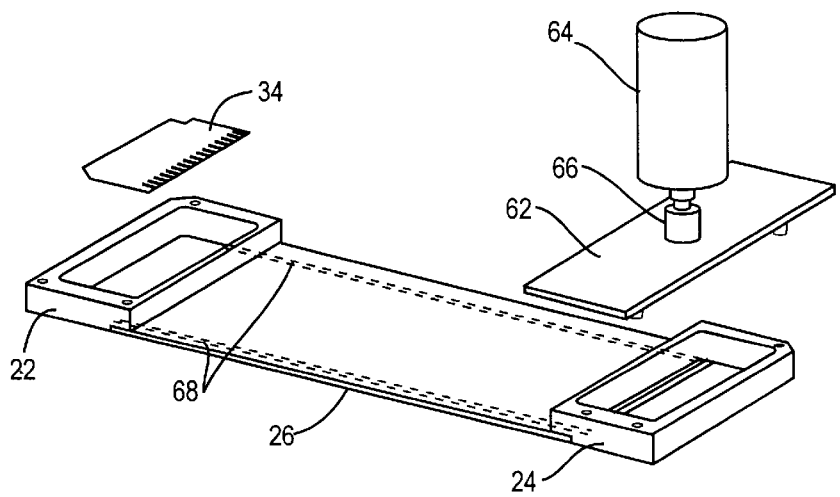
FIG. 3 is a perspective view depicting preparation of the cassette for two-dimensional separation.

FIG. 3 shows one method by which a cassette 20 may be filled with a separation medium. Reservoirs 22, 24 are provided with removable caps or covers 62. Caps 62 have inlets to allow introduction of a medium into the reservoirs. The prepared separation medium is injected into reservoir 24 by a syringe pump 64 having a nozzle 66. As compartments 22, 24 and 26 are fluidly connected, the mixture fills the ultra-thin space between the glass plates of compartment 26 and also fills the reservoirs to a desired level.

Once filled into the cassette, the separation medium was solidified at room temperature for approximately fifteen minutes. Then, an injection hole was punched into the right side of the solidified medium using a pipette tip. One $\mu$l of alpha lactalbumin ($\alpha$LA), one $\mu$l of ovalbumin (OVA), and 1 $\mu$l of bovine serum albumin (BSA), all at one mg/ml concentration, were dissolved in an SDS sample buffer (60 mM Tris-HCl, 1% SDS, 5 mM mercaptoethanol) and boiled at 100° C. for five minutes. The protein mixture was cooled in ice water to room temperature, and one $\mu$l of bromophenol blue at a concentration of 0.001 mg/ml was added to the protein mixture. The protein mixture was then injected into the punched hole in the right side of the solidified separation medium.

Figure 4:
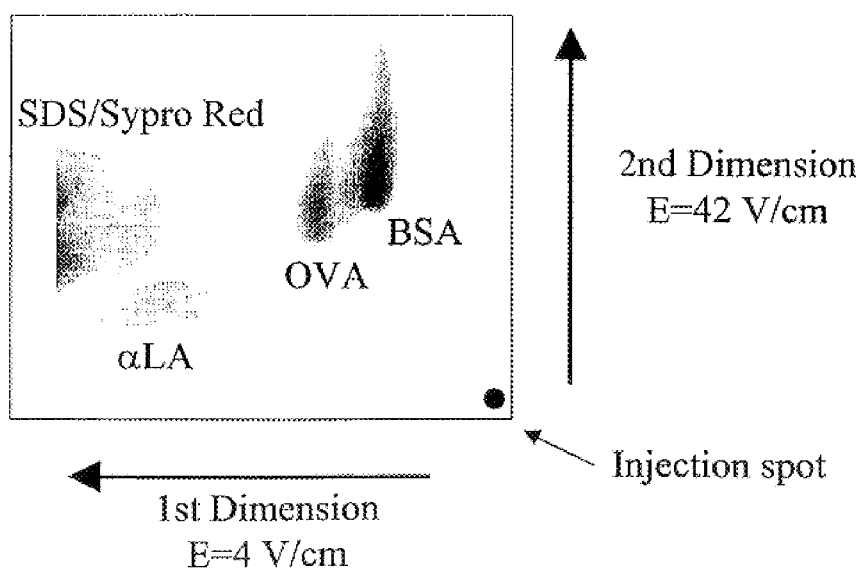
FIG. 4 is a two-dimensional map showing the results of a sample two-dimensional separation according to the present invention.

A 4 V/cm electric field was applied to the first dimension electrodes (configured as shown in FIG. 2a) to commence first dimension separation. The electric field was applied until the bromophenol blue band migrated to the other (left) side of the reservoir. The power supply was then disconnected from the IEF reservoir and connected across the second dimension separation compartment as shown in FIG. 2b. A 42 V/cm electric field was applied to initiate second dimension separation. As the SDS protein complexes migrated into the second dimension separation medium towards the anode, they were complexed with the Sypro Red labeling dye. As the complexed proteins passed through area 39, the fluorescent labeling dye was illuminated by the beam from the illuminating fiber of the apparatus and the emitted light collected by the collecting fibers and relayed to computer 80 for analysis. FIG. 4 is a two-dimensional image map generated by computer 80 showing separation of the three-protein test mixture into distinct areas of $\alpha$LA, OVA and BSA.

While particular embodiments of the present invention have been described above, it should be understood that they have been presented by way of example only, and not as limitations. The breadth and scope of the present invention is defined by the following claims and their equivalents, and is not limited by the particular embodiments described herein.

What is claimed is:

1. An automated and integrated proteome analyzer comprising:
    a separation cassette for providing multi-dimensional separation of a proteinaceous sample, wherein the cassette includes
        a first dimension separation compartment housing a material having capillary channels, the proteinaceous sample being disposed in the capillary channels for first dimension separation;
        a second dimension separation compartment housing a separation medium, the separation medium receiving the proteinaceous sample for second dimension separation; and
        a power supply configured to apply an electric field across either the first dimension compartment or the second dimension compartment;
    an illumination and detection system positioned adjacent the second dimension separation compartment for illuminating and detecting the separated proteinaceous sample during second dimension separation; and
    an analysis system for processing data received from the illumination and detection system and formatting the data into a two-dimensional map representing the separated proteinaceous sample.

2. An analyzer as claimed in claim 1, and further comprising a material for creating a pH gradient disposed in the first dimension separation compartment.

3. An analyzer as claimed in claim 1, wherein the material having capillary channels is a porous membrane.

4. An analyzer as claimed in claim 1, wherein the material having capillary channels is an inert matrix.

5. An analyzer as claimed in claim 4, wherein the inert matrix is agarose.

6. An analyzer as claimed in claim 1, wherein the second dimension separation compartment comprises two planes of a transparent material separated by a separation medium.

7. An analyzer as claimed in claim 6, wherein the transparent material is selected from a group consisting of glass and plastic.

8. An analyzer as claimed in claim 6, wherein the separation medium is a thin layer of a linear polymer suspended in an inert matrix.

9. An analyzer as claimed in claim 8, wherein the linear polymer has a concentration of less than twenty-five percent, and is selected from a group consisting of non-cross linked polyacrylamide, dextran, polyethylene oxides, derivatized celluloses, polyvinylpyrrolidone and mixtures thereof.

10. An analyzer as claimed in claim 8, wherein the inert matrix is selected from a group consisting of agarose and micro-lithographic arrays.

11. An analyzer as claimed in claim 8, wherein the thickness of the layer is less than 0.2 millimeters.

12. An analyzer as claimed in claim 6, and further comprising a staining dye disposed in the separation medium.

13. An analyzer as claimed in claim 12, wherein the staining dye is a dye capable of complexing with the proteinaceous sample.

14. An analyzer as claimed in claim 13, wherein the staining dye is selected from a group consisting of Ethidium Bromide, Nile Red, Sypro Orange or Sypro Red.

15. An analyzer as claimed in claim 1, wherein the illumination and detection system is an integrated fiber optics-based, laser-induced fluorescence detection system.

16. An analyzer as claimed in claim 15, wherein the illumination and detection system comprises:
    a laser for emitting an illuminating beam;
    a lens set for focusing the illuminating beam on the detection area;
    an excitation fiber for transmitting the illuminating beam from the laser to the lens set;
    a translation stage for oscillating the lens set over the detection area;
    collection fibers for collecting fluorescent light emitted by the separated proteinaceous sample; and
    an avalanche photodiode detector for receiving the collected fluorescent light.

17. An analyzer as claimed in claim 1, wherein the illumination and detection system comprises a CCD camera-based hyper-spectral imaging system.

18. An analyzer as claimed in claim 1, wherein the analysis system is a PC having data analysis software.

19. A separation cassette for providing two-dimensional separation comprising:

first and second reservoirs, wherein the first reservoir is a first dimension separation compartment and contains a porous material having capillary channels, a proteinaceous sample disposed in the porous material, and a pH gradient;

a second dimension separation compartment fluidly connected to the first and second reservoirs, the second dimension compartment comprising two glass or plastic plates separated by an ultra-thin layer of a linear polymer suspended in an inert matrix; and a power supply configured to apply an electric field across either the first reservoir to effect isolectric focusing or across the second dimension separation compartment to effect separation by a sieving effect.

20. A separation cassette as claimed in claim 19 in combination with an illumination and detection system and an analysis system, the illumination and detection system comprising:

a laser for emitting an illuminating beam;

a lens set for focusing the illuminating beam on a detection area of the second dimension separation compartment;

an excitation fiber for transmitting the illuminating beam from the laser to the lens set;

a translation stage for oscillating the lens set over the detection area;

collection fibers for collecting fluorescent light emitted by the separated proteinaceous sample; and an avalanche photodiode detector for receiving the collected fluorescent light and supplying data to the analysis system.

21. A method for analyzing a proteinaceous sample by two dimensional separation comprising:

(a) disposing the proteinaceous sample in a material having capillary channels;

(b) disposing a material having a pH gradient in the capillary channels;

(c) applying a first electric field to the material to effect a first dimension separation by isoelectric focusing of components of the proteinaceous sample;

(d) contacting the material containing the focused proteinaceous sample with a separation medium;

(e) applying a second electric field to the separation medium to effect a second dimension separation of the proteinaceous sample;

(f) fluorescently labeling the proteinaceous sample, wherein a staining dye incorporated into the separation medium forms a complex with the proteinaceous sample;

(g) illuminating the fluorescently labeled sample;

(h) collecting light emitted by the fluorescently labeled sample; and (i) analyzing the collected light and formatting a two-dimensional image map corresponding to the separated proteinaceous sample.

22. A method as claimed in claim 21, wherein in step (a), the proteinaceous sample is absorbed into a porous membrane having capillary channels.

23. A method as claimed in claim 22, wherein in step (b), the pH gradient is absorbed into the porous membrane.

24. A method as claimed in claim 23, wherein in step (d), the porous membrane is contacted with a separation medium comprising a linear polymer suspended in an inert matrix.

25. A method as claimed in claim 21, wherein in step (a), the proteinaceous sample is injected into an inert matrix having capillary channels.

26. A method as claimed in claim 21, and further comprising the step of fluorescently labeling the proteinaceous sample before second dimension separation.

27. A method for analyzing a proteinaceous sample by two dimensional separation comprising:

(a) disposing the proteinaceous sample in a material having capillary channels;

(b) disposing a material having a pH gradient in the capillary channels;

(c) applying a first electric field to the material to effect a first dimension separation by isoelectric focusing of components of the proteinaceous sample;

(d) contacting the material containing the focused proteinaceous sample with a separation medium;

(e) applying a second electric field to the separation medium to effect a second dimension separation of the proteinaceous sample;

(f) fluorescently labeling the proteinaceous sample;

(g) illuminating the fluorescently labeled sample using a laser beam transmitted by an illuminating fiber of a fiber optics bundle;

(h) collecting light emitted by the fluorescently labeled sample with transmission fibers that transmit the collected light to an avalanche photodiode detector; and (i) analyzing the collected light and formatting a two-dimensional image map corresponding to the separated proteinaceous sample;

wherein steps (g) and (h) are preformed simultaneously with step (e).

28. A method for analyzing a proteinaceous sample by two dimensional separation comprising:

(a) disposing the proteinaceous sample in a material having capillary channels;

(b) disposing a material having a pH gradient in the capillary channels;

(c) applying a first electric field to the material to effect a first dimension separation by isoelectric focusing of components of the proteinaceous sample;

(d) contacting the material containing the focused proteinaceous sample with a separation medium;

(e) before step (f), labeling a first portion of the proteinaceous sample with a first fluorescent die;

(f) applying a second electric field to the separation medium to effect a second dimension separation of the proteinaceous sample;

(g) after step (f), labeling the proteinaceous sample with a second fluorescent die in order to provide a means for distinguishing the first portion of the proteinaceous sample;

(g) illuminating the fluorescently labeled sample;

(h) collecting light emitted by the fluorescently labeled sample; and (i) analyzing the collected light and formatting a two-dimensional image map corresponding to the separated proteinaceous sample.

29. A method for analyzing a proteinaceous sample by two dimensional separation comprising:

(a) disposing the proteinaceous sample in a material having capillary channels;

(b) disposing a material having a pH gradient in the capillary channels;

(c) applying a first electric field to the material to effect a first dimension separation by isoelectric focusing of components of the proteinaceous sample;

(d) contacting the material containing the focused proteinaceous sample with a separation medium;

(e) applying a second electric field to the separation medium to effect a second dimension separation of the proteinaceous sample;

(f) fluorescently labeling the proteinaceous sample;

(g) illuminating the fluorescently labeled sample;

(h) collecting light emitted by the fluorescently labeled sample; and (i) analyzing the collected light and formatting a two-dimensional image map corresponding to the separated proteinaceous sample;

wherein steps (g) and (h) are performed simultaneously with step (e).

* * * * *